United States Patent [19]

Franz et al.

[11] Patent Number: 5,015,481
[45] Date of Patent: May 14, 1991

[54] STABILIZED PHARMACEUTICAL ADMIXTURE COMPOSITION

[75] Inventors: Michel Franz; Michel Jans, both of Brussels, Belgium; Leo K. Mathur, Vernon Hills; Kamlesh B. Shah, Arlington Heights; James E. Truelove, Libertyville, all of Ill.

[73] Assignee: G. D. Searle & Co., Chicago, Ill.

[21] Appl. No.: 518,354

[22] Filed: May 3, 1990

[51] Int. Cl.$^5$ .................. A61K 9/00; A61K 45/08
[52] U.S. Cl. .................. 424/494; 514/781; 514/970
[58] Field of Search ............ 424/494; 514/781, 970

[56] References Cited

U.S. PATENT DOCUMENTS

| | | | |
|---|---|---|---|
| 3,903,297 | 9/1975 | Robert | 514/530 |
| 4,092,425 | 5/1978 | Stringfellow | 514/530 |
| 4,113,882 | 9/1978 | Okazaki et al. | 514/572 |
| 4,301,146 | 11/1981 | Sanvordeke | 514/530 |
| 4,666,716 | 5/1987 | Sheth et al. | 424/195.1 |
| 4,678,516 | 7/1987 | Alderman et al. | 424/488 |
| 4,695,464 | 9/1987 | Alderman | 514/781 |
| 4,797,286 | 1/1989 | Thakkar | 424/456 |
| 4,847,092 | 7/1989 | Thakkar | 424/456 |
| 4,867,979 | 9/1989 | Sheth et al. | 424/195.1 |
| 4,874,757 | 10/1989 | Crawford | 514/226.5 |
| 4,889,720 | 12/1989 | Konishi | 424/435 |
| 4,943,587 | 7/1990 | Cetenko et al. | 514/415 |
| 4,968,505 | 11/1990 | Okada et al. | 424/494 |

FOREIGN PATENT DOCUMENTS 8656761 10/1987 Australia.

OTHER PUBLICATIONS

James et al., Hyperalgesia after Treatment of Mice with etc., Arzneimittelforschung, 28, 804-7, 01/78.
Mikami et al., The Potentiating Effects of Prostaglandins on etc., J. Pharm. Pharmacol., 31, 856-7, 01/79.
Walter et al., Effects of Analgesics on Bradykin-Induced etc., Agents and Actions, 27, 375-7, 01/79.
Taiwo et al., Prostaglandins Inhibit Endogenous Pain Control etc., J. Neurosci., 8, 1346-9, 01/88.
Pateromichelakis et al., Prostaglandin E1-Induced Sensitization of Aa etc., Brain Research, 232, 89-96, 01/82.
Sanyal et al., Prostaglandins: Antinociceptive Effect of etc., Clin. Exp. Pharmacol. Physiol., 4, 247-55, 01/77.
Bhattacharya et al., Potentiation of Antinociceptive Action of etc., Clin. Exp. Pharmacol. Physiol., 2, 353-357, 01/75.
Ferri et al., Decreased Antinociceptive Effect of Morphine etc., Psychopharmacologia, 39, 231-5, 01/74.
Sanyal et al., The Antinociceptive Effect of etc., Psychopharmacology, 60, 159-63, 01/79.
G. D. Searle & Co., Cytotec (Misoprostol) Drug Information, Physician's Desk Reference, 44, 2056-7, 01/90.
IMS, IMS Marketletter, IMS Marketletter, 06/87.
Myamoto et al., CA-106:182704v (1987).
Shah et al., CA-107:141114e (1987).
Euro-Celtique CA-107:161685y (1987).
Mizukami CA-107:223298g (1987).
Mizukami et al., CA-110:63743e (1988).
Vyas et al., CA-112:42452k (1989).
Okada et al., CA-113:65269r (1990).
Igura et al., CA-110:219072y (1988).

Primary Examiner—Shep K. Rose
Attorney, Agent, or Firm—Paul D. Matukaitis; Roger A. Williams

[57] ABSTRACT

A stabilized pharmaceutical composition which is an admixture of an NSAID selected from diclofenac and piroxicam, a prostaglandin and hydroxypropyl methylcellulose for maintaining the prostaglandin in a therapeutically effective amount without negatively affecting the therapeutic activity of the NSAID.

8 Claims, No Drawings

STABILIZED PHARMACEUTICAL ADMIXTURE COMPOSITION

BACKGROUND OF THE INVENTION

The invention herein is directed to a stabilized pharmaceutical composition which consists of an admixture of an NSAID selected from diclofenac and piroxicam, a prostaglandin such as will be described hereinafter in more detail and a stabilizer for maintaining the prostaglandin in a therapeutically effective amount without negatively affecting the therapeutic activity of the NSAID.

Nonsteroidal anti inflammatory drugs (NSAIDs) comprise a class of drugs which have long been recognized as having high therapeutic value especially for the treatment of inflammatory conditions such as are found in inflammatory diseases like osteoarthritis (OA) and rheumatoid arthritis (RA). While the NSAIDs present a beneficial therapeutic value they can exhibit undesirable side effects. An especially undesirable side effect of the administration of NSAIDs is the ulcerogenic effects generally associated with chronic use. In chronic use of NSAIDs, use of high dosages of NSAIDs and especially the use of NSAIDs by the elderly can lead to NSAID induced ulcers. NSAID induced ulcers in the stomach can be dangerous. Such ulcers generally exhibit little or few symptoms and may cause dangerous bleeding when undetected. The United States Food and Drug Administration requires a class warning for the use of NSAID's which states: Serious gastrointestinal toxicity such as bleeding, ulceration, and perforation can occur at any time, with or without warning symptoms, in patients treated chronically with NSAID therapy.

Certain prostaglandins have been shown to prevent NSAID induced ulcers. Acceptable prostaglandin compounds for use in the invention herein and their preparations are described in U.S. Pat. Nos. 3,965,143, 4,060,691, 4,271,314 and 4,683,328. The prostaglandin compound commercially available under the USAN (United States Adopted Name) name misoprostol is a pharmaceutically acceptable prostaglandin which has been accepted for use in the treatment of NSAID induced ulcers in many countries, including the United States. Misoprostol is commercially available by prescription in such countries.

While prostaglandins are beneficial compounds and have found therapeutic usage, prostaglandins are generally considered highly unstable and difficult to provide in orally available stabilized form. Therefore it is desirable to find prostaglandins which can be stabilized or be provided in stabilized formulations. It would also be desirable to provide such a prostaglandin in an orally available form.

It would be desirable to provide a pharmaceutical composition which would exhibit the beneficial properties of an NSAID and which composition could exhibit the beneficial properties of a prostaglandin for countering (by inhibiting, reducing and/or preventing) the undesirable side effect of NSAID induced ulcer formation due to NSAID administration.

SUMMARY OF THE INVENTION

The invention herein is directed to a stabilized pharmaceutical composition which includes an admixture of an NSAID selected from diclofenac and piroxicam, a prostaglandin such as will be described hereinafter in more detail and a stabilizer for maintaining the prostaglandin in a therapeutically effective amount without negatively affecting the therapeutic activity of the NSAID. The prostaglandin preferably is an orally available prostaglandin. Acceptable prostaglandins for use herein include prostaglandins having the following structure

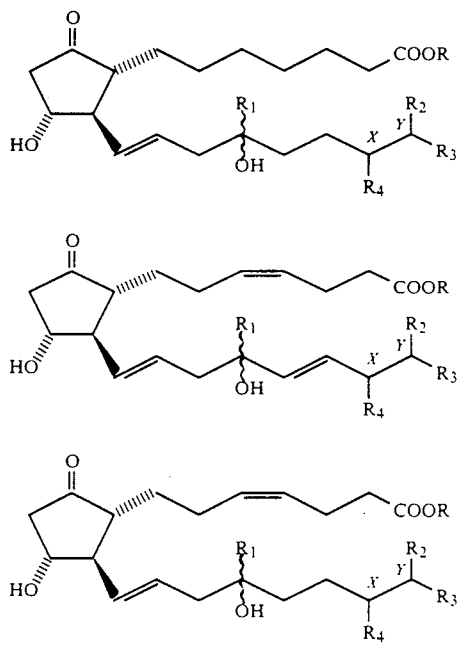

wherein R represents hydrogen or lower alkyl having 1 to 6 carbon atoms, $R_1$ represents hydrogen, vinyl or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cycloalkenyl having 4 to 6 carbon atoms or $R_3$ and $R_4$ together with carbons X and Y form a cycloalkenyl having 4 to 6 carbon atoms and wherein the X-Y bond can be saturated or unsaturated.

An especially preferred pharmaceutical composition herein comprises the NSAID diclofenac in a therapeutic amount such as from 25 to 75 mg, misoprostol in a therapeutic amount from 100 to 200 micrograms (mcg) and the stabilizer hydroxypropyl methylcellulose (HPMC) in an amount from about 10 to 100 mg.

DETAILED DESCRIPTION OF THE INVENTION

The invention herein is directed to a stabilized pharmaceutical composition which consists of an admixture of an NSAID selected from diclofenac and piroxicam, a prostaglandin such as will be described hereinafter in more detail and a stabilizer for maintaining the prostaglandin in a therapeutically effective amount without negatively affecting the therapeutic activity of the NSAID. The prostaglandin preferably is an orally available prostaglandin. Acceptable prostaglandins for use herein include prostaglandins having the following structure

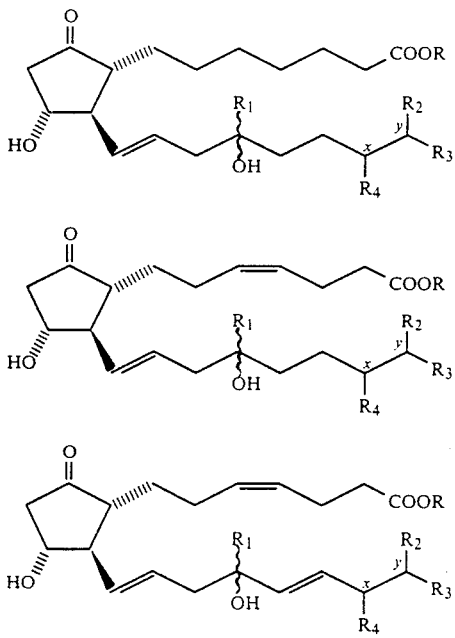

wherein R represents hydrogen or lower alkyl having 1 to 6 carbon atoms, $R_1$ represents hydrogen, vinyl or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cycloalkenyl having 4 to 6 carbon atoms or $R_3$ and $R_4$ together with carbons X and Y form a cycloalkenyl having 4 to 6 carbon atoms and wherein the X-Y bond can be saturated or unsaturated.

The pharmaceutical composition herein includes an NSAID selected from diclofenac, piroxicam and their pharmaceutically acceptable salts.

The NSAID can be present in any therapeutically acceptable amount. If the NSAID is diclofenac, for normal dosing of diclofenac, diclofenac is administered in a dosing range from 25 mg to 75 mg per tablet. The Physicians' Desk Reference, 44th Edition, states that the recommended dosage for osteoarthritis is 100 to 150 mg per day in divided doses. For rheumatoid arthritis the recommended dosage is 150 to 200 mg per day in divided doses. For ankylosing spondylitis the recommended dosage is 100 to 125 mg per day in divided doses. The pharmaceutical composition herein can include an amount from 25 to 75 mg of diclofenac, and preferably a dosage of 50 mg. Various excipients can be combined with the diclofenac as is well known in the pharmaceutical art provided such excipients do not exhibit a destabilizing effect on the prostaglandin.

If the NSAID is piroxicam, the piroxicam can be present in a therapeutically acceptable amount. Currently commercially available piroxicam capsules contain either 10 mg or 20 mg of piroxicam. The PDR, 44th Edition, recommends that piroxicam be administered in a single daily dose of 20 mg for rheumatoid arthritis and osteoarthritis. The pharmaceutical composition herein preferably contains from 10 to 20 mg of piroxicam. Various excipients can be present, provided such excipients do not exhibit a destabilizing effect on either the piroxicam or the prostaglandin.

The terms "prostaglandin" and/or its accepted acronym "PG" or, as more appropriately for the E-series prostaglandins, "PGE," are used herein to refer to naturally occurring or man-made E-series prostaglandins and their analogs and derivatives.

It has been found herein that prostaglandins useful herein include the $E_1$ prostaglandins shown by the following Formula I

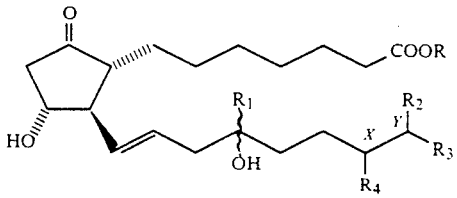

$E_2$ prostaglandins shown by the following Formula II

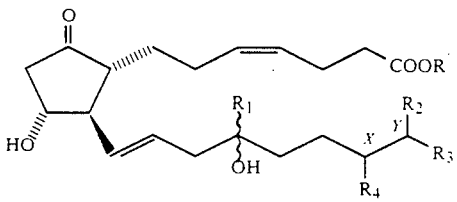

and $E_3$ prostaglandins shown by the following Formula III

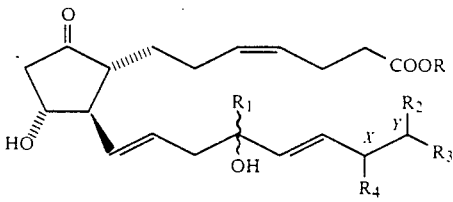

wherein R represents hydrogen or lower alkyl having 1 to 6 carbon atoms, $R_1$ represents hydrogen, vinyl or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cycloalkenyl having 4 to 6 carbon atoms or $R_3$ and $R_4$ together with carbons X and Y form a cycloalkenyl having 4 to 6 carbon atoms and wherein the X-Y bond can be saturated or unsaturated.

By lower alkyl is meant straight o branched chain alkyl such as methyl, ethyl, propyl, isopropyl, butyl, secondary butyl or tertiary butyl, pentyl, or hexyl with the indicated limitation of the number of carbon atoms. The bond between carbon X and carbon Y can be saturated or unsaturated.

It has been found herein that prostaglandins useful herein include misoprostol, (±)methyl 11α,16-dihydroxy-16-methyl-9-oxoprost 13E-en-1-oate, represented by the following Formula:

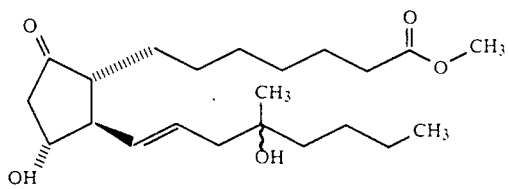

the prostaglandin enisoprost, (±) methyl 11α,16-dihydroxy 16-methyl-9-oxoprosta-4Z,13E-diene-1-oate represented by the following Formula:

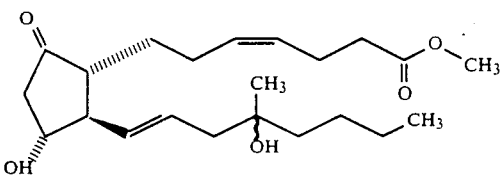

and the prostaglandin methyl 7-[2B-[6-(1-cyclopenten-1-yl)-4-hydroxy-4-methyl-1E,5E-hexadienyl]-3α-hydroxy-5-oxo1R,1α-cyclopentyl]-4Z-heptenoate represented by the following Formula:

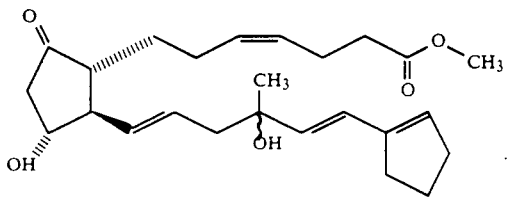

With regard to the illustrated structures, the dashed line indicates the grouping being behind the plane of the paper and the solid, blackened triangular shape indicates that the group is in front of the plane of the paper.

The prostaglandins useful in the composition of the invention herein can be prepared by known reaction schemes such as by the methods taught in U.S. Pat. Nos. 3,965,143; 4,271,314; and 4,683,328. The individual isomers can be obtained by chromatographic separation. The prostaglandin is preferably an orally available prostaglandin.

When the prostaglandin is misoprostol, (±)methyl 11α,16 dihydroxy 16 methyl-9-oxoprost-13E-en-1-oate, the misoprostol is present in an amount of about 100 to 200 mcg (micrograms).

The stabilizing agent that is used in the formulation herein is hydroxypropyl methylcellulose (HPMC). It has been found that HPMC provides an especially useful stabilizing effect on the prostaglandins in the presence of diclofenac or piroxicam. Studies of an admixture of diclofenac and misoprostol have shown that misoprostol is highly unstable and degrades very readily and at a relatively fast rate. Studies have shown that HPMC can lessen the antiinflammatory activity of diclofenac. Surprisingly, the admixture herein of misoprostol, diclofenac and HPMC did not lessen the antiinflammatory activity of the diclofenac even though a relatively high amount of HPMC is present as is required to stabilize the misoprostol. That is, the diclofenac in the admixture exhibited an antiinflammatory activity comparable to diclofenac alone as if no HPMC had been present. Further, the misoprostol present in the admixture was sufficiently stable to support the admixture as a viable, commercial pharmaceutical product.

It has been found herein that the HPMC in the admixture is present in an amount sufficient to stabilize the misoprostol present in the admixture. The amount of HPMC depends upon the amount of diclofenac present and the amount of misoprostol present in the admixture. The amounts of these two active ingredients can vary as herein described depending on the indication for which the admixture is indicated. Generally, the HPMC is present in the admixture in range of about 10 mg to about 100 mg. A particularly preferred amount of HPMC is an amount that is from 50 to about 500 times the amount by weight of prostaglandin present in the admixture and especially an amount from 15 to about 30 mg. The amount of HPMC also depends upon consideration of the route of administration. For example, if the admixture is formed into a tablet the tablet should be designed for ease of swallowing.

The invention will be further described with regard to the following examples.

EXAMPLE 1

A pharmaceutical composition is prepared consisting of diclofenac, misoprostol and the stabilizer HPMC having the following composition.

| Ingredient | Unit Formula (mg) |
| --- | --- |
| diclofenac | 50.0 |
| lactose (monohydrate) | 13.0 |
| microcrystalline cellulose | 12.9 |
| cornstarch | 8.4 |
| povidone K-30 | 4.8 |
| magnesium stearate | 0.9 |
| purified water | |
| misoprostol | 0.2 |
| hydroxypropyl methylcellulose | 20.0 |
| crospovidone | 10.0 |
| colloidal silicon dioxide | 0.5 |
| hydrogenated castor oil | 1.0 |
| microcrystalline cellulose | 233.3 |

EXAMPLE 2

A pharmaceutical composition admixture was prepared consisting of diclofenac sodium, misoprostol and HPMC which had the following composition.

| Ingredient | Unit Formula (mg) |
| --- | --- |
| diclofenac sodium | 50.0 |
| lactose (monohydrate) | 13.0 |
| microcrystalline cellulose | 12.9 |
| cornstarch | 8.4 |
| povidone K-30 | 4.8 |
| magnesium stearate | 0.9 |
| purified water | |
| misoprostol:HPMC dispersion (1:100) | |
| misoprostol | 0.2 |
| hydroxypropyl methylcellulose | 20.0 |
| crospovidone | 10.0 |
| colloidal silicon dioxide | 0.5 |
| hydrogenated castor oil | 1.0 |
| microcrystalline cellulose | 233.3 |

EXAMPLE 3

A pharmaceutical composition admixture is prepared consisting of piroxicam, enisoprost and HPMC which has the following composition.

| Ingredient | Weight % Formulation |
| --- | --- |
| piroxicam | 10.00 |
| lactose (anhydrous) | 42.00 |
| microcrystalline cellulose | 42.00 |
| sodium lauryl sulfate | 0.50 |
| magnesium stearate | 0.50 |
| enisoprost:HPMC dispersion (1:99) | |
| enisoprost | 0.05 |
| hydroxypropyl methylcellulose | 4.95 |

EXAMPLE 4

A pharmaceutical composition admixture was prepared consisting of piroxicam, enisoprost and HPMC which had the following composition.

| Ingredient | Weight % Formulation |
| --- | --- |
| piroxicam | 10.00 |
| lactose (anhydrous) | 42.15 |
| microcrystalline cellulose | 42.15 |
| sodium lauryl sulfate | 0.20 |
| magnesium stearate | 0.50 |
| enisoprost:HPMC dispersion (1:99) | |
| enisoprost | 0.05 |
| hydroxypropyl methylcellulose | 4.95 |

EXAMPLE 5

The composition of Example 2 was evaluated on an accelerated stability study. The composition was evaluated for sixteen weeks at 40° C. The composition was assayed at the end of the sixteen week period to determine the amount of misoprostol remaining in the composition. The assay was performed using a stability indicating high performance liquid chromatography (HPLC) assay method. The HPLC assay was performed on column packed with DuPont RP8, 15 cm ×4.6 mm i.d. The mobile phase was acetonitrile/methanol/water (24/40/35 v/v/v) and the flow rate was 1.5 ml/min. The injection volume was 100 mcl and detection was monitored at 200 nm and 280 nm with a run time of 20 min.

The composition of Example 2 exhibited a viable stability as 90 percent of the misoprostol remained after 16 weeks at the temperature of 40° C.

The composition that is the invention herein provides an ease of delivery of an NSAID for its therapeutic value such as the alleviation of inflammation in a delivery system which limits the undesirable side affect of ulcerogenesis brought about by such NSAID therapy. That is, the composition herein provides a prostaglandin in combination with the NSAID whereby the prostaglandin can be administered for its beneficial therapeutic value in preventing and/or inhibiting the incidence of NSAID induced ulcers.

A particularly beneficial aspect of the invention herein is that the combination of the two components in a single unit dosage such as a single tablet assures compliance with the therapeutic regimen of the two active components. That is, a co administration of the active components (NSAID and prostaglandin) separately can be difficult to achieve as it can be difficult for a patient to faithfully follow a co administration regimen. By combining the two active components in the same tablet or composition, adherence to the therapeutic regimen is controlled as the administration of the tablet containing the NSAID assures compliance of the administration of the prostaglandin present in the same tablet.

The composition herein is especially utile as the composition herein exhibits a stability for the prostaglandin and the NSAID in such a fixed combination as herein described while maintaining the therapeutic property, such as antiinflammatory activity, of the NSAID.

We claim:

1. A stabilized oral and pharmaceutical composition comprising, in admixture, an NSAID selected from diclofenac, piroxicam and their salts; a prostaglandin having the following structure;

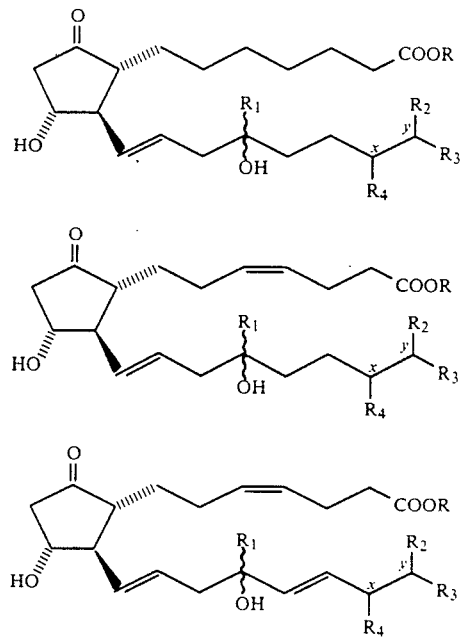

wherein R represents hydrogen or lower alkyl having 1 to 6 carbon atoms, $R_1$ represents hydrogen, vinyl or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cycloalkenyl having 4 to 6 carbon atoms or $R_3$ and $R_4$ together with carbons X and Y form a cycloalkenyl having 4 to 6 carbon atoms and wherein the X-Y bond can be saturated or unsaturated; and hydroxypropyl methylcellulose in an amount from about 10 mg to about 100 mg.

2. A stabilized pharmaceutical composition as recited in claim 1 wherein the prostaglandin comprises misoprostol.

3. A stabilized composition as recited in claim 2 wherein the NSAID comprises diclofenac.

4. A stabilized composition as recited in claim 2 wherein the NSAID comprises piroxicam.

5. A stabilized pharmaceutical composition as recited in claim 2 wherein the hydroxypropyl methylcellulose is present in an amount from about 15 mg to about 30 mg.

6. A stabilized pharmaceutical composition as recited in claim 1 wherein the prostaglandin comprises misoprostol in an amount from about 100 mcg to about 200 mcg, the NSAID comprises diclofenac in an amount from about 25 mg to about 75 mg, and the hydroxypropyl methylcellulose is present in an amount from about 15 mg to about 30 mg.

7. A stabilized pharmaceutical composition as recited in claim 6 wherein the misoprostol is present in an amount of about 200 mcg, the diclofenac is present in an amount of about 50 mg and the HPMC is present in an amount of about 20 mg.

8. A method of treating inflammation comprising administering to a patient in need of such treatment a therapeutically effective amount of the stabilized pharmaceutical composition according to claim 1.

* * * * *

UNITED STATES PATENT AND TRADEMARK OFFICE
CERTIFICATE OF CORRECTION

PATENT NO. : 5,015,481

DATED : May 14, 1991

INVENTOR(S) : Franz et al.

It is certified that error appears in the above-identified patent and that said Letters Patent is hereby corrected as shown below:

Column 7, line 53, reading "to faithfully follow a co admin-instration" should read -- to faithfully follow a co-administration --.

Signed and Sealed this

Fifteenth Day of December, 1992

*Attest:*

DOUGLAS B. COMER

*Attesting Officer*      *Acting Commissioner of Patents and Trademarks*